United States Patent [19]

Honda et al.

[11] Patent Number: 5,113,880
[45] Date of Patent: May 19, 1992

[54] DENTAL FLOSS AND INTERDENTAL CLEANING TOOL

[75] Inventors: Narimichi Honda, Yamaguchi; Kazuo Yagi, Ohtake, both of Japan

[73] Assignee: Mitsui Petrochemical Industries, Ltd., Tokyo, Japan

[21] Appl. No.: 553,346

[22] Filed: Jul. 17, 1990

Related U.S. Application Data

[63] Continuation of Ser. No. 343,419, Apr. 26, 1989, abandoned.

[30] Foreign Application Priority Data

Apr. 26, 1988 [JP] Japan ................. 63-103180
Apr. 26, 1988 [JP] Japan ................. 63-103181

[51] Int. Cl.⁵ .................................. A61C 15/00
[52] U.S. Cl. .................................... 132/321
[58] Field of Search ............. 132/321, 323, 325

[56] References Cited

U.S. PATENT DOCUMENTS

| | | | |
|---|---|---|---|
| 2,981,264 | 4/1961 | De Felice | 132/323 |
| 3,783,883 | 1/1974 | Alexander | 132/323 |
| 4,013,085 | 3/1977 | Wright | 132/323 |
| 4,545,950 | 10/1985 | Motooka et al. | 264/210.6 |
| 4,583,564 | 4/1986 | Finkelstein et al. | 132/321 |
| 4,646,766 | 3/1987 | Stallard | 132/321 |

FOREIGN PATENT DOCUMENTS

| | | | |
|---|---|---|---|
| 118695 | 7/1944 | Australia | 132/321 |
| 0052353 | 5/1982 | European Pat. Off. | |
| 0172671 | 2/1986 | European Pat. Off. | |
| 2922824 | 12/1979 | Fed. Rep. of Germany | 132/323 |

*Primary Examiner*—John J. Wilson
*Attorney, Agent, or Firm*—Sherman and Shalloway

[57] ABSTRACT

A dental floss having excellent tensile strength, impact strength, water resistance, creep resistance and use feeling and composed of a drawn multifilament of an ultrahigh-molecule-weight polyolefin having an intrinisic viscosity of at leasat 5 dl/g or an ultrahigh-molecular-weight ethylene-alpha-olefin copolymer containing an alpha-olefin having at least 3 carbon atoms in an amount of 0.1 to 20 on an average per 1000 carbon atoms. An interdental cleaning tool comprising the dental floss stretched taut between protruding portions of the tool is also provided.

30 Claims, 1 Drawing Sheet

DENTAL FLOSS AND INTERDENTAL CLEANING TOOL

This application is a continuation of application Ser. No. 07/343,419 filed Apr. 26, 1989, now abandoned.

BACKGROUND OF THE INVENTION

1. Field of the Invention

This invention relates to a dental floss, and more specifically, to a dental floss composed of a multifilament of an ultrahigh-molecular-weight polyolefin or an ultrahigh-molecular-weight ethylene/alpha-olefin copolymer and having excellent tensile strength, impact strength, water resistance, creep resistance and use feeling.

This invention also relates to an interdental cleaning tool, and more specifically, to an interdental cleaning tool comprising a taut dental floss composed of a multifilament of an ultrahigh-molecular-weight polyolefin or an ultrahigh-molecular-weight ethylene/alpha-olefin copolymer and having excellent tensile strength, impact strength, water resistance, creep resistance and use feeling.

2. Description of the Prior Art

The dental floss is used to remove food residues or the like between teeth by inserting it therebetween and pulling it strongly with fingers through the teeth.

The conventional dental floss is composed of a crimped nylon multifilament. Since, however, the nylon dental floss has low tensile strength or impact strength, it is frequently broken during use, and it is impossible to clean all interdental parts in the mouth with one dental floss. Furthermore, since it has poor self-lubricating property, it is liable to be caught by teeth and gives an uncomfortable feel of use.

Accordingly, it has been desired to develop a dental floss having excellent tensile strength, impact strength, creep resistance and use feeling.

It has already been known to mold ultrahigh-molecular-weight polyethylene into fibers and tapes, and stretch them to molecularly oriented products having high moduli and tensile strengths. For example, Japanese Laid-Open Patent Publication No. 15408/1981 describes that a dilute solution of ultrahigh-molecular-weight polyethylene is spun and the resulting filament is drawn. Japanese Laid-Open Patent Publication No. 130313/1984 describes that ultrahigh-molecular-weight polyethylene and a wax are melt-kneaded, and the mixture is extruded, cooled and solidified and thereafter stretched. Japanese Laid-Open Patent Publication No. 187614/1984 states that the above molten mixture is extruded, subjected to drafting, cooled and solidified and then stretched.

SUMMARY OF THE INVENTION

It is an object of this invention to provide a dental floss having excellent tensile strength, impact strength, creep resistance, water resistance and use feeling.

Another object of this invention is to provide an interdental cleaning tool which is easy to use and comprises a taut dental floss having excellent tensile strength, impact strength, creep resistance, water resistance and self-lubricating property.

The first object is achieved in accordance with this invention by a dental floss composed of a drawn multifilament of an ultrahigh-molecular-weight polyolefin having an intrinsic viscosity $[\eta]$ of at least 5 dl/g.

The first object is also achieved in accordance with this invention by a dental floss composed of a drawn multifilament of an ultrahigh-molecular-weight ethylene/alpha-olefin copolymer having an intrinsic viscosity $[\eta]$ of at least 5 dl/g and containing an alpha-olefin having at least 3 carbon atoms in an amount of 0.1 to 20 on an average per 1000 carbon atoms.

The second object is achieved in accordance with this invention by an interdental cleaning tool comprising a dental floss composed of a drawn multifilament of an ultrahigh-molecular-weight polyolefin having an intrinsic viscosity $[\eta]$ of at least 5 dl/g stretched taut between protruding portions of the tool spaced from each other by a predetermined distance.

The second object is also achieved in accordance with this invention by an interdental cleaning tool comprising a dental floss composed of a drawn multifilament of an ultrahigh-molecular-weight ethylene/alpha-olefin copolymer having an intrinsic viscosity $[\eta]$ of at least 5 dl/g and containing an alpha-olefin having at least 3 carbon atoms in an amount of 0.1 to 20 on an average per 1000 carbon atoms, said dental floss being stretched taut between protruding parts of the tool spaced from each other by a predetermined distance.

BRIEF DESCRIPTION OF THE DRAWING

The accompanying drawing.

DESCRIPTION OF THE PREFERRED EMBODIMENTS

Figure 1:
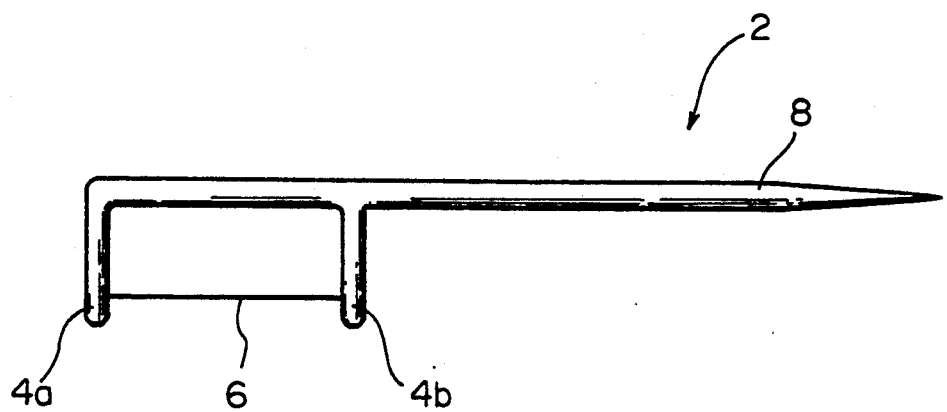
FIG. 1, is a schematic view showing an interdental cleaning tool in accordance with one embodiment of the invention, in which the interdental cleaning tool 2 is comprised of a handle portion 8 and a dental floss 6 stretched taut between projecting parts 4a and 4b.

The first dental floss of this invention is composed of a drawn multifilament of an ultrahigh-molecular-weight polyolefin having an intrinsic viscosity $[\eta]$ of at least 5 dl/g. The second dental floss in accordance with this invention is composed of a drawn multifilament of an ultrahigh-molecular-weight ethylene/alpha-olefin copolymer having an intrinsic viscosity $[\eta]$ of at least 5 dl/g and containing an alpha-olefin having at least 3 carbon atoms in an amount of 0.1 to 20 on an average per 1000 carbon atoms.

The dental flosses of this invention are composed of a drawn multifilament of the ultrahigh-molecular-weight polyolefin or ethylene/alpha-olefin copolymer, and have excellent tensile strength, impact strength, creep resistance and water resistance. Thus, even when they are inserted and passed between teeth by pulling them strongly, they do not undergo breakage. Furthermore, since they have good self-lubricating property as the inherent property of the polyolefin, they are not caught by the teeth and have an excellent use feeling.

The interdental cleaning tool of this invention is characterized basically by the fact that a dental floss is stretched taut between its protruding portions of the tool spaced from each other by a predetermined distance, and that the dental floss is composed of a drawn multifilaments of an ultrahigh-molecular-weight polyolefin having an intrinsic viscosity of at least 5 dl/g or a drawn multifilament of an ultrahigh-molecular-weight ethylene/alpha-olefin copolymer containing an alpha-olefin having at least 3 carbon atoms in an amount of 0.1 to 20 on an average per 1000 carbon atoms.

The dental floss stretched taut in the interdental cleaning tool of this invention is composed of a drawn multifilament of the ultrahigh-molecular-weight polyolefin or ethylene/alpha-olefin copolymer and has excellent tensile strength, impact strength, creep resistance, water resistance and self-lubricating property. Accordingly, this dental floss can be stretched taut strongly between protruding parts of the interdental cleaning tool. Even when this dental floss is inserted between teeth and passed therethrough, it does not undergo breakage, and further has excellent use feeling because of its inherent self-lubricating property.

The dental flosses of this invention will be described below in detail.

The drawn filament of the ultrahigh-molecular-weight polyolefin and the drawn filament of the ultrahigh-molecular-weight ethylene/alpha-olefin copolymer which constitute the dental flosses of this invention will be described.

Specific examples of the ultrahigh-molecular-weight polyolefin constituting the drawn filament used in this invention are ultrahigh-molecular-weight polyethylene, ultrahigh-molecular-weight polypropylene, ultrahigh-molecular-weight poly-1-butene and ultrahigh-molecular-weight copolymers of two or more alpha-olefins. The drawn filament of the ultrahigh-molecular-weight polyolefin has excellent tensile strength, impact strength, creep resistance and water resistance.

The ultrahigh-molecular-weight ethylene/alpha-olefin copolymer constituting the drawn filament used in this invention may be an ultrahigh-molecular-weight copolymer of ethylene with at least one alpha-olefin selected from alpha-olefins having 3 to 20 carbon atoms, preferably 4 to 10 carbon atoms, for example, ultrahigh-molecular-weight ethylene/propylene copolymer, ultrahigh-molecular-weight ethylene/1-butene copolymer, ultrahigh-molecular-weight ethylene/propylene/1-butene copolymer, ultrahigh-molecular-weight ethylene/4-methyl-1-pentene copolymer, ultrahigh-molecular-weight ethylene/1-hexene copolymer, ultrahigh-molecular-weight ethylene/1-octene copolymer or ultrahigh-molecular-weight ethylene/1-decene copolymer. The ultrahigh-molecular-weight ethylene/alpha-olefin copolymers containing at least one alpha-olefin having at least 3 carbon atoms in an amount of 0.1 to 20, preferably 0.5 to 10, more preferably 1 to 7, on an average per 1000 carbon atoms.

Drawn filaments obtained from such ultrahigh-molecular-weight ethylene/alpha-olefin copolymers have better impact strength and creep resistance than a drawn filament obtained from ultrahigh-molecular-weight polyethylene.

The ultrahigh-molecular-weight polyolefin or ethylene/alpha-olefin copolymer constituting the drawn filament used in this invention has an intrinsic viscosity of at least 5 dl/g, preferably 7 to 30 dl/g, and drawn filaments obtained from these ultrahigh-molecular-weight polymers or copolymers have excellent mechanical properties and thermal resistance. The molecular ends of these polymers do not contribute to the filament strength, and the number of molecular ends is a reciprocal of the molecular weight (viscosity). Polymers with higher intrinsic viscosities give higher strength.

The density of the drawn filaments used in this invention have a density of 0.940 to 0.990 g/cm$^3$, preferably 0.960 to 0.985 g/cm$^3$. The density is measured by a density gradient tube method in accordance with a conventional method (ASTM D1505). At this time, the density gradient tube is prepared by using carbon tetrachloride and toluene, and the measurement is made at room temperature (23° C.).

The drawn filaments used in this invention have a dielectric constant (1 KHz, 23° C.) of 1.4 to 3.0, preferably 1.8 to 2.4 and a dielectric loss tangent (1 KHz, 80° C.) of 0.05 to 0.008%, preferably 0.040 to 0.010%. The dielectric constant and dielectric loss tangent are measured in accordance with ASTM D150 using a sample obtained aligning molecularly oriented articles in fiber or tape form densely in one direction to render them in film form.

The drawn filaments used in this invention have a draw ratio of 5 to 80, preferably 10 to 50.

The degree of molecular orientation in the drawn filaments used in this invention may be determined by X-ray diffractometry, a birefringence method or a fluorescent polarizing method. From the viewpoint of mechanical properties, the drawn filaments are desirably oriented molecularly so that the degree of orientation (F) defined by the following equation becomes at least 0.90, especially at least 0.95.

$$\text{Degree of orientation } (F) = \frac{90° - H°/2}{90°}$$

In the equation, H° is the half-value width (°) of the intensity distribution curve along the Debye ring of the most intense paratroope surface on the equatorial line.

The above degree of orientation is described in detail, for example, in Yukichi Go and Kiichiro Kubo: Kogyo Kagaku Zasshi, vol. 39, page 992 (1939).

The drawn filaments used in this invention have excellent mechanical properties, and show a modulus of at least 20 GPa, especially at least 30 GPa, and a tensile strength of at least 1.2 GPa, especially at least 1.5 GPa.

The drawn filaments used in this invention have an impulse voltage breakdown of 110 to 250 KV/mm, preferably 150 to 220 KV/mm. The impulse voltage breakdown is measured on the same sample as used in measuring the dielectric constant by applying impulses of a negative polarity at 2 KV/3 steps by a JIS-type electrode of brass (25 mm⌀).

The drawn filament of the ultrahigh-molecular-weight ethylene/alpha-olefin copolymer used in this invention has excellent impact strength, breakdown energy and creep resistance. The characteristics of this filament are expressed by the following properties.

The drawn filament of the ultrahigh-molecular-weight ethylene/alpha-olefin copolymer used in this invention has a breakdown of at least 8 kg-m/g, preferably at least 10 kg-cm/g.

The drawn filament of the ultrahigh-molecular-weight ethylene/alpha-olefin copolymer has excellent creep resistance, and partially outstanding creep resistance at high temperatures corresponding to room temperature creep resistance under accelerated conditions. It has a creep, determined as an elongation (%) after 90 seconds under a 30% fracture load at an ambient temperature of 70° C., of not more than 7%, especially not more than 5%. It has a creep speed ($\epsilon$, sec$^{-1}$) after the lapse of 80 seconds from 90 seconds, of not more than $4 \times 10^{-4}$ sec$^{-1}$, especially $5 \times 10^{-5}$ sec$^{-1}$. These room temperature properties of the drawn filament of the ultrahigh-molecular-weight ethylene/alpha-olefin copolymer can be further improved, and also it attains excellent thermal resistance, if it has the following thermal properties as well.

The drawn filament of the ultrahigh-molecular-weight ethylene/alpha-olefin copolymer used in this invention has a heat of fusion of at least 15%, preferably at least 20%, especially preferably at least 30% based on at least one crystal fusion peak (Tp) existing at a temperature at least 20° C. higher than the inherent crystal melting temperature (Tm) of the copolymer.

The crystal fusion temperature (Tm) inherent to the ultrahigh-molecular weight ethylene/alpha-olefin copolymer can be determined by a method which comprises completely melting the drawn filament, then cooling it to relax the molecular orientation of the drawn filament and then again heating the filament, namely, by a second run in a differential scanning calorimeter.

More specifically, in the drawn filaments used in this invention, no crystal fusion peak exists in the inherent crystal fusion temperature zone of the copolymer. Even if it exists, it is only as a slight tailing. Generally, the crystal fusion peak (Tp) appears usually in a temperature range $Tm+20°$ C. to $Tm+50°$ C., especially a temperature range of $Tm+20°$ C. to $Tm+100°$ C. In many cases, a plurality of peaks Tp appear within the above temperature range. Frequently, the crystal fusion peaks Tp appear as a higher temperature side fusion peak ($Tp_1$) in the temperature range of $Tm+35°$ C. to $Tm+100°$ C., and a lower temperature side fusion peak ($Tp_2$) in the temperature range of $Tm+20°$ C. to $Tm+35°$ C. Depending upon the conditions for producing the drawn filament, $TP_1$ or $Tp_2$ may be composed of a plurality of peaks.

These high crystal fusion peaks ($Tp_1$, $Tp_2$) appear to increase the heat resistance of the drawn filament of the ultrahigh-molecular weight ethylene/alpha-olefin copolymer markedly, and to contribute to the high strength retention or modulus retention of the filaments after it has been subjected to high temperatures.

The total sum of the amount of fusion heat based on the high-temperature side fusion peak ($Tp_1$) in the temperature range of $Tm+35°$ C. to $Tm+100°$ C. is at least 1.5%, especially at least 3.0%, based on the total amount of heat of fusion.

So long as the total amount of heat of fusion based on the high-temperature side fusion peak ($Tp_1$) satisfies the above value, even when the high-temperature side fusion peak ($Tp_1$) does not appear projectingly as a main peak, namely even when it becomes an assembly or small peaks or a broad peak, the filament retains excellent creep resistance characteristics although its thermal resistance might be reduced to some extent.

The melting point and the amount of heat of crystal fusion are measured by the following methods.

The melting point is measured by a differential scanning calorimeter by the following procedure. A differential scanning calorimeter of model DSCII (made by Perkin Elmer Co.) is used. About 3 mg of the sample filament is sound about an aluminum plate having a size of 4 mm × 4 mm × 0.2 mm thickness to restrain it in the oriented direction. The sample wound around the aluminum plate was enclosed in an aluminum pan to prepare a measuring sample. The same aluminum plate as used in the sample is enclosed in a usually empty aluminum pan put in a reference holder to create a thermal balance. The sample was first maintained at 30° C. for about 1 minute, and then heated to 250° C. at a temperature elevating rate of 10° C./min , and the melting point of the sample in the first temperature elevation was measured. Subsequently, the sample was maintained at 250° C. for 10 minutes and then cooled at a temperature lowering speed of 20° C./min and further maintained at 30° C. for 10 minutes. Then, the sample was heated for the second time at a temperature elevation rate of 10° C./min , and the melting point was measured during the second temperature elevation (second run). The maximum value of the fusion peak is defined as the melting point. When the peak appears as a shoulder, a tangent line is drawn at the deflection point immediately on the lower temperature side of the shoulder and at the deflection point immediately on the higher temperature side of the shoulder, and the intersecting point of the tangent lines is defined as the melting point.

The points at 60° C. and 240° C. in the endothermic curve are connected, and perpendiculars are drawn to this straight line (base line) and a point 20° C. higher than the inherent crystal fusion temperature (Tm) of the ultrahigh-molecular weight ethylene copolymer, and a low temperature side surrounded by these is regarded as being based on the inherent crystal fusion (Tm) of the ultrahigh-molecular-weight ethylene copolymer, and the high temperature portion is regarded as being based on the crystal fusion (Tp) which results in expressing the function of the drawn filament. The amounts of heat of crystal fusion of these portions were calculated from the areas of these. The amounts of heat of fusion based on $TP_1$ and $TP_2$ were also calculated as above. Specifically, a portion enclosed by a perpendicular from $Tm+20°$ C. and a perpendicular from $Tm+35°$ C. is regarded as the amount of heat of fusion based on the fusion of $TP_2$, and the high temperature portion, as the amount of heat of fusion based on the fusion of $TP_1$.

The drawn filament of the ultrahigh-molecular-weight ethylene/alpha-olefin copolymer of this invention has a strength retention of at least 95% and a modulus elasticity retention of at least 90%, especially at least 95%, after it is subjected to a heat history at 170° C. for 5 minutes, and thus shows excellent thermal resistance not at all seen in drawn filaments of conventional polyethylenes.

Process for producing a molecularly oriented molded article of the ultrahigh-molecular-weight polyolefin The stretched article of the ultrahigh-molecular-weight polyolefin having high modulus and tensile strength can be obtained, for example, by methods described in Japanese Laid-Open Patent Publications Nos. 15408/1981, 5228/1983, 130313/1984 and 187614/1984, in which the ultrahigh-molecular-weight polyolefin is formed into a dilute solution, or a low-molecular-weight compounds such as a paraffinic wax is added to the ultra-high-molecular-weight polyolefin to improve the stretchability of the ultrahigh-molecular-weight polyolefin.

Process for producing a molecularly oriented molded article of the ultrahigh-molecular-weight ethylene/alpha-olefin copolymer (1) Starting material The ultrahigh-molecular-weight ethylene/alpha-olefin copolymer used in this invention can be obtained, for example, by slurry polymerization of ethylene and at least one alpha-olefin having at least 3 carbon atoms in an organic solvent in the presence of a Ziegler catalyst.

Examples of the alpha-olefin having at least 3 carbon atoms are propylene, butene-1, pentene-1, 4-methylpentene-1, hexene-1, heptene-1 and octene-1. Butene-1, 4-methylpentene-1, hexene-1, and octene-1 are preferred. One or more alpha-olefins are copolymerized with ethylene so that it will be present in an amount of 0.1 to 20 on an average per 1000 carbon atoms of the resulting copolymer.

The ultrahigh-molecular-weight ethylene/alpha-olefin copolymer used as the starting material for the molecularly oriented molded article of the invention should have a molecular weight corresponding to the intrinsic viscosity mentioned above.

The alpha-olefin component in the ultrahigh-molecular-weight ethylene/alpha-olefin copolymer used in this invention is determined by means of an infrared spectrophotometer (made by Nippon Bunko Kogyo Co., Ltd.). Specifically, the absorbance at 1378 cm$^{-1}$ representing the deformation vibration of the methyl group of the alpha-olefin taken up in the ethylene chain is measured by an infrared spectrophotometer. This value is applied to a calibration curve prepared by a $^{13}$C nmr device using a model compound, and the number of methyl branches per 1000 carbon atoms is roughly calculated. Consequently, the amount of alpha-olefin in the ultrahigh-molecular-weight ethylene/alpha-olefin copolymer is determined.

(2) Production process

To produce a molecularly oriented article from the ultrahigh-molecular-weight ethylene/alpha-olefin copolymer, a diluent is first added to the copolymer. Various waxy substances having compatibility with the copolymer are used as the diluent.

Examples of the waxes as the diluent include aliphatic hydrocarbons and derivatives thereof. Such aliphatic hydrocarbons are composed mainly of saturated aliphatic hydrocarbons, and are called paraffinic waxes having a molecular weight of not more than 2,000, preferably not more than 1,000.

Specific examples of such aliphatic hydrocarbons include n-alkanes having at least 22 carbon atoms such as docosane, tricosane, tetracosane and triacontane, mixtures of these alkanes with a minor proportion of lower n-alkanes, paraffin wax isolated and purified from petroleum, medium to low pressure polyethylene Waxes which are low-molecular-weight polymers obtained by polymerizing ethylene or ethylene and another alpha-olefin, high-pressure method polyethylene wax, ethylene copolymer wax, waxes obtained by decreasing the molecular weights of polyethylenes such as medium-to-low pressure method polyethylene and high pressure-method polyethylene by thermal degradation, oxidized products of these waxes, and modification products of these waxes with maleic acid.

The aliphatic hydrocarbon derivatives may be aliphatic alcohols, fatty acid amides, fatty acid esters, aliphatic mercaptans, aliphatic aldehydes and aliphatic ketones which have at least 8 carbon atoms, preferably 12 to 50 carbon atoms, and a molecular weight of 130 to 2,000, preferably 200 to 800, and contain 1 or more, preferably 1 to 2, especially preferably 1, functional group such as a carboxyl, hydroxyl, carbamoyl, ester, mercapto or carbonyl group.

Specific examples of such aliphatic hydrocarbon include fatty acids such as capric acid, lauric acid, myristic acid, palmitic acid, stearic acid and oleic acid, aliphatic alcohols such as lauryl alcohol, fatty acid amides such as capramide, lauramide, palmitamide and stearylamide, and fatty acid esters such as stearylacetic ester.

The weight ratio of the ultrahigh-molecular-weight ethylene/alpha-olefin copolymer to the diluent is generally from 3:97 to 80:20, particularly from 15:85 to 60:40 although it may vary depending upon the types of these compounds. If the amount of the diluent is lower than the specified limit, the melt viscosity of the copolymer becomes too high and it is difficult to melt-knead or melt-mold. The resulting molded article has a heavily roughened surface and is liable to undergo breakage upon stretching. On the other hand, if the amount of the diluent is larger than the above specified limit, melt kneading of the copolymer becomes difficult, and the stretchability of the molded article is reduced.

Melt-kneading is carried out generally at 150 to 300° C., particularly 170° to 270° C. At temperatures lower than the specified lower limit, the melt viscosity of the copolymer is too high, and it is difficult to melt-mold. If it is higher than the specified upper limit, the molecular weight of the ultrahigh-molecular-weight ethylene/alpha-olefin copolymer, and it is difficult to obtain a molded article having high modulus and strength. Compounding may be carried out by the dry method using a Henschel mixer, a V-type blender, etc., or by using a single-screw extruder or a multi-screw extruder.

Melt-molding of a dope composed of the ultra-high-molecular-weight ethylene/alpha-olefin copolymer and the diluent is carried out generally by melt extrusion. Specifically, the dope is melt-extruded through a spinneret to obtain an undrawn filament. The molten extrudate extruded from the spinneret may be elongated in the molten state by applying a draft. The ratio of the extrusion speed $V_0$ of the molten resin within a die orifice to the speed $V$ of taking up the cooled and solidified undrawn article is called a draft ratio and expressed by the following equation.

$$\text{Draft ratio} = V/V_0 \qquad (2)$$

The draft ratio may vary depending upon the temperature of the mixture and the molecular weight of the ultrahigh-molecular-weight ethylene/alpha-olefin copolymer. It may be usually at least 3, preferably at least 6.

The undrawn molded article of the ultrahigh-molecular-weight ethylene/alpha-olefin copolymer is then subjected to a drawing treatment. Drawing is performed so that molecular orientation in at least one direction will be effectively imparted to the undrawn molded article from the ultrahigh-molecular-weight ethylene/alpha-olefin copolymer.

The drawing is carried out at a temperature of generally 40° to 160° C., especially 80° to 145° C. Air, steam and a liquid medium may be used as a heat medium for maintaining the undrawn molded article at the above temperatures. It is preferred to use a liquid medium which is a solvent for dissolving and removing the diluent and has a boiling point higher than the melting point of the molded article, specifically decalin, decane or kerosene because the diluent can be removed and the drawing can be achieved at a high draw ratio without causing drawing non-uniformity.

The diluent may be removed from the ultrahigh-molecular-weight ethylene/alpha-olefin copolymer by other means. For example, it may be performed by treating the undrawn article with a solvent such as hexane, heptane, hot ethanol, chloroform or benzene, or by treating the drawn article with a solvent such as hexane, heptane, hot ethanol, chloroform or benzene. As a result, a drawn product having high modulus and strength can be obtained.

The drawing operation may be carried out in one step or in a multiplicity of steps. The draw ratio is generally 5 to 80, preferably 10 to 50, although it may depend upon the desired molecular orientation and the incidental effect of increasing the melting temperature.

Generally, it is preferred to carry out the drawing in a multiplicity of staps. Preferably, in the first step, the extruded molded article is drawn at a relatively low temperature of 80° to 120° C. while the diluent is being extracted from the molded article, and in the second and subsequent steps, the molded article is drawn at a temperature of 120° to 160° C. which is higher than the drawing temperature in the first step.

Monoaxial drawing may be carried out by drawing the molded article between rollers having different peripheral speeds.

The resulting drawn filament may be heat-treated as desired under restrained conditions. The heat-treatment may be carried out at a temperature of generally 140° to 180° C., preferably 150° to 175° C., for 1 to 20 minutes, preferably 3 to 10 minutes. Crystallization of the oriented crystalline portion further proceeds as a result of the heat-treatment thereby to cause shifting of the crystalline fusion temperature to a higher temperature side, increase strength and modulus and improved creep resistance at higher temperatures.

In this invention a plurality (usually 5 to 300) of such drawn filaments of the ultrahigh-molecular weight polyolefin or ethylene/alpha-olefin copolymer are bundled to form a drawn multifilament, which is used as a dental floss. Waxes may be used at this time to prevent the monofilament from separating into the individual filaments. A perfume such as mint may be used to improve its use feeling.

EFFECTS OF THE INVENTION

Since the dental floss of this invention is composed of the drawn multifilament of the ultrahigh-molecular-weight polyolefin or ethylene/alpha-olefin copolymer, it has excellent tensile strength, impact strength, creep resistance, water resistance and self-lubricating property. Accordingly, when the dental floss of this invention is inserted between teeth and pulled strongly to permit passage therebetween, it does not break, and moreover, it has an excellent use feeling. The dental floss composed of the drawn multifilament is easy to insert between teeth, and spreads between teeth to permit thorough cleaning.

In the interdental cleaning tool of this invention, the drawn multifilament of the ultrahigh-molecular-weight polyolefin or ethylene/alpha-olefin copolymer is used as a dental floss stretched taut over projecting portions of the interdental cleaning tool. Since the dental floss of this invention has excellent tensile strength, impact strength, creep resistance, water resistance and self-lubricating property, it does not break when inserted between teeth and pulled strongly to permit passage between teeth. Moreover, this dental floss has an excellent use feeling. Furthermore, the dental floss composed of the drawn multifilament is flat and easy to insert between teeth, and moreover spreads between teeth to permit thorough cleaning. Furthermore since the dental floss has an excellent tensile strength, it can be stretched over the protruding portions of the interdental cleaning tool while it is pulled strongly. It does not loosen nor break during use, and can be used very conveniently.

The interdental cleaning tool of this invention will be described with reference to FIG. 1 which is a rough view of one embodiment of the interdental cleaning tool of this invention.

As shown in FIG. 1, the interdental cleaning tool 2 of this invention has a rod-like handle portion 8 and rod-like protruding portions 4a and 4b protruding nearly at right angles to the handle portion 8. The angle between the protruding portion 4a or 4b may be changed according to the site of using the interdental cleaning tool. One protruding portion 4a is formed at the forward end portion of the handle portion 8 and the other protruding portion 4b is spaced from the protruding portion 4a by a predetermined distance. The distance between the protruding portions 4a and 4b should be formed in a larger width than the tooth thickness of a general person, preferably 10 to 30 mm. The protruding portions 4a and 4b and the handle portion 8 are preferably formed as a one-unit piece from a synthetic resin.

The dental floss is stretched taut between the protruding portions. To stretch the dental floss and fix it to the protruding portions 4a and 4b, such means as bonding and engagement may be used. Preferably it is provided replaceably because, the replacement of the dental floss becomes easy. The forward end of the handle portion 8 is preferably sharpened to make it function as a toothpick.

The following examples illustrate the present invention without any intention of limiting the scope of the invention thereby.

REFERENTIAL EXAMPLE 1

Production of an ultrahigh-molecular weight ethylene/butene-1 copolymer

Ethylene and butene-1 were copolymerized in slurry in 1 liter of n-decane as a polymerization solvent in the presence of a Ziegler-type catalyst. A gaseous monomeric mixture composed of ethylene and butene-1 in a mole ratio of 97.2:2.35 was continuously fed into a reactor so that the pressure is maintained constant at 5 kg/cm$^2$. At a reaction temperature of 70° C., the polymerization ended in 2 hours.

The amount of the ultrahigh-molecular-weight ethylene/butene-1 copolymer powder obtained was 160 g. The copolymer had an intrinsic viscosity, measured in decalin at 135° C., of 8.2 dl/g and contained butene-1 in an amount of 1.5 per 1000 carbon atoms as measured by an infrared spectrophotometer.

Preparation of a drawn oriented article of the ultrahigh-molecular weight ethylene/butene-1 copolymer A mixture of 20 parts by weight of the resulting ultrahigh-molecular-weight ethylene/butene-1 copolymer powder and 80 pars of a paraffin wax (melting point=69° C. and molecular weight=490) was melt-spun under the following conditions.

One hundred parts by weight of the mixture was mixed with 0.1 part by weight of 3,5-di-tert-butyl-4-hydroxytoluene as a process stabilizer. The mixture was melt-kneaded at a set temperature of 190° C. by using a screw-type extruder (screw diameter of 25 mm, L/D=25; made by Thermoplastics Co., Ltd.). Subsequently, the molten mixture was melt-spun from a spinning die having an orifice diameter of 2 mm attached to the extruder. The extruded molten mixture was taken up at a draft ratio of 36 through an air gap of 180 cm, and cooled and solidified in the air to obtain an undrawn filament. The undrawn filament was drawn under the following conditions.

The undrawn filament was stretched in two steps by using the three godet rolls. n-Decane was used as a heat medium in the first drawing tank, and the temperature of the heat medium was 110° C. Ethylene glycol was used as a heat medium in the second drawing tank, and its temperature was 145° C. The effective length of each of the first and second drawing tanks was 50 cm. The rotating speed of the first godet roll was adjusted to 0.5 m/min., and by changing the rotating speed of the third godet roll, an oriented filament with a desired draw ratio was obtained. The rotating speed of the second godet roll was properly chosen within those speeds which permit stable drawing. Almost all of the parafin wax initially mixed with the copolymer was extracted into n-decane during drawing.

The oriented filament was then washed with water, and dried at room temperature under reduced pressure for one days. The properties of the drawn filament were measured by the following methods. The draw ratio was calculated from the ratio of the rotating speed of the first godet roll to that of the third godet roll.

Tensile properties

Modulus and tensile strength were measured at 23° C. by using a tensile tester (model DCS-59, made by Shimazu Seisakusho Co., Ltd.).

At this time, the length of the sample between clamps was 100 mm, and the pulling speed was 100 mm/min. (100%/min., distortion speed). The modulus is an initial modulus calculated by using the inclination of the tangent line. The cross-sectional area of the filament required for calculation was calculated from the weight of the filament using 0.960 g/cc as its density.

Retentions of modulus and tensile strength affer heat history

The heat history test was carried out by leaving the sample to stand in a Geer's oven (Perfect Oven made by Tabai Seisakusho).

The sample was fixed at both ends to a device comprised of a stainless steel frame and a plurality of pulleys provided at both ends of the frame. The both ends of the sample were fixed to such an extent as not to cause loosening of the sample, and no tension was positively exerted on the sample. The tensile properties after the heat history were measured as described in the section of Tensile properties.

Creep resistance

The creep resistance was measured by a thermal stress-strain measuring device (TMA/SS10, made by Seiko Electronics Industry Co., Ltd.). The sample length was 1 cm, and the ambient temperature was 70° C., and the test was carried out under a load corresponding to 30% of the fracture load at room temperature. To quantitatively evaluate the amount of creep, the following two values were determined, namely the creep elongation (%) $CR_{90}$ measured when a load was exerted on the sample, and 90 seconds passed, and the average creep speed ($sec^{-1}$) $\epsilon$ after the lapse of 80 seconds from the end of this 90 second period.

The tensile properties of a multifilament obtained by bundling a multiplicity of the drawn oriented filaments are shown in Table 1.

TABLE 1

| | |
|---|---|
| Sample: | sample 1 |
| Filament: | 1000 denier/100 |
| Draw ratio: | 22.3 |
| Strength: | 2.4 GKPa |
| Modulus: | 60 GPa |
| Elongation: | 5.50% |
| Degree of orientation (F.): | 0.975 |

The inherent crystal fusion peak of the drawn filament of the ultrahigh-molecular-weight ethylene/butene-1 copolymer was 126.7° C., and the proportion of Tp based on the area of the total crystal fusion peak was 33.8%. The creep resistance characteristics were $CR_{90}=3.1\%$, $\epsilon=3.03\times10^{-5}$. After a heat history at 170° C. for 5 minutes, the drawn filament had a modulus of 102.2%, and a tensile strength retention of 102.5%, showing no reduction in these properties by heat history.

The amount of work required for the breakage of the drawn filament was 10.3 kg.cm/g. The drawn filament had a density of 0.973 g/cm$^3$, a dielectric constant of 2.2, a dielectric loss tangent of 0.024%, and an impulse voltage breakdown of 180 KV/mm.

REFERENTIAL EXAMPLE 2

Production of an ultrahigh-molecular-weight ethylene/octene-1 copolymer

Ethylene and octene-1 were polymerized in slurry in 1 liter of n-decane as a polymerization solvent in the presence of a Ziegler-type catalyst. As a comonomer, 125 ml of octene-1 and 40 Nml of hydrogen for molecular weight adjustment were all added before the start of the polymerization, and then the polymerization was started. Ethylene gas was continuously fed so that the pressure in the reactor was maintained constant at 5 kg/cm$^2$. The polymerization ended in 2 hours at 70° C.

The amount of the ultrahigh-molecular-weight ethylene/octene-1 copolymer powder obtained was 178 g. The copolymer had an intrinsic viscosity measured at 135° C. in decalin of 10.66 dl/g and contained octene-1 in an amount of 0.5 per 1000 carbon atoms when measured by an infrared spectrophotometer.

Preparation and properties of a drawn oriented article of the ultrahigh-molecular-weight ethylene/octene-1 copolymer A drawn oriented filament was prepared from the above copolymer by the method described in Referential Example 1. A plurality of the resulting drawn oriented filaments were bundled, and the tensile properties of the resulting multifilament are shown in Table 2.

TABLE 2

| | |
|---|---|
| Sample: | sample 2 |
| Filament: | 1000 denier/100 |
| Draw ratio: | 16.0 |
| Strength: | 2.3 GPa |
| Modulus: | 65 GPa |
| Elongation: | 5.40% |
| Degree of orientation (F.): | 0.978 |

The inherent crystal fusion peak of the drawn filament (sample 2) of the ultrahigh-molecular-weight ethylene/octene-1 copolymer was 132.1° C., and the proportions of Tp and $Tp_1$ based on the area of the total crystal fusion peak were 97.7% and 5.0%, respectively. The creep resistance characteristics of sample 2 were $CR_{90}=32.0\%$ and $\epsilon=9.50\times10^{-6}$ sec$^{-1}$. After a heat history at 170° C. for 5 minutes, the drawn filament had a modulus retention of 108.2%, and a tensile strength retention of 102.1%.

The amount of work required for the breakage of the drawn filament was 10.1 kg.cm/g. The drawn filament had a density of 0.971 g/cm$^3$, a dielectric constant of 2.2, a dielectric loss tangent of 0.031%, and an impulse voltage breakdown of 185 KV/mm.

REFERENTIAL EXAMPLE 3

A mixture of 20 parts by weight of ultrahigh-molecular-weight polyethylene (homopolymer) powder having an intrinsic viscosity, measured in decalin at 135° C., of 7.42 dl/g and 80 parts by weight of a parafin wax (melting point=69° C., molecular weight=490) was melt-spun and drawn by the same method as described in Referential Example 1 to give a drawn oriented filament. A multifilament was prepared by bundling a multiplicity of the resulting drawn oriented filaments. The tensile properties of the multifilament are shown in Table 3.

TABLE 3

| | |
|---|---|
| Sample: | sample 3 |
| Filament: | 1000 denier/100 |
| Draw ratio: | 23.1 |
| Strength: | 2.5 GPa |
| Modulus: | 90 GPa |
| Elongation: | 4.10% |
| Degree of orientation (F.): | 0.980 |

The inherent crystal fusion peak of the drawn filament (sample 3) of the ultrahigh-molecular-weight polyethylene was 135.1° C., and the proportion of Tp based on the area of the total crystal fusion peak was 8.8%. Likewise, the proportion of the higher-temperature side peak $Tp_1$ based on the total crystal fusion peak area was less than 1%. The creep resistance characteristics of sample 3 were $CR_{90}=11.9\%$ and $\epsilon=1.07\times 10^{-3} sec^{-1}$. After a heat history at 170° C. for 5 minutes, the drawn filament had a modulus retention of 80.4%, and a tensile strength retention of 78.2%.

The amount of work of sample 3 required for breakage was 6.8 kg.m/g, and the sample 3 had a density of 0.985 g/cm$^3$, a dielectric constant of 2.3, a dielectric loss tangent of 0.030%, and an impulse voltage breakdown of 182 KV/mm.

EXAMPLE 1

A handle portion 8 and protruding portions 4a and 4b as shown in FIG. 1 were produced as a one-piece unit from polyethylene (Ultozex 20100J produced by Mitsui Petrochemical Industries, Ltd.). The drawn multifilament prepared in Referential Example 1 was stretched taut between the protruding portions 4a and 4b as a dental floss, interdental cleaning was carried out actually by using the resulting tool. The multifilament was very strong, and after cleaning interdental parts of all the teeth in the mouth, practically no monofilament breakage occurred, and it retained its function completely.

The multifilament was very seldom caught by the teeth during cleaning as compared with conventional dental flosses, and showed an excellent use feeling.

EXAMPLE 2

The drawn multifilament produced in Referential Example 2 was mounted on an interdental cleaning tool produced in the same way as in Example 1, and used in interdental cleaning. The multifilament was very strong, and after cleaning interdental parts of all the teeth in the mouth, practically no monofilament breakage occurred, and it retained its function completely.

The multifilament was very seldom caught by the teeth during cleaning as compared with conventional dental flosses, and showed an excellent use feeling.

EXAMPLE 3

The drawn multifilament produced in Referential Example 3 was mounted on an interdental cleaning tool produced in the same way as in Example 1, and use in interdental cleaning. The multifilament was very strong, and after cleaning interdental parts of all the teeth in the mouth, practically no monofilament breakage occurred, and it retained its function completely.

The multifilament was very seldom caught by the teeth during cleaning as compared with conventional dental flosses, and showed an excellent use feeling.

We claim:

1. A dental floss composed of a drawn multifilament of an ultrahigh-molecular-weight polyolefin having an intrinsic viscosity of at least 5 dl/g.

2. The dental floss of claim 1 wherein the drawn multifilament is drawn at a draw ration of 5 to 80.

3. The dental floss of claim 1 or 2 in which the ultrahigh-molecular-weight polyolefin is ultrahigh-molecular-weight polyethylene.

4. The dental floss of claim 1 in which the polyethylene has an intrinsic viscosity of 7 to 30 dl/g.

5. A dental floss composed of a drawn multifilament of an ultrahigh-molecular-weight ethylene/alpha-olefin copolymer having an intrinsic viscosity of at least 5 d/g and containing at least one alpha-olefin having at least 3 carbon atoms in an amount of 0.1 to 20 on an average per 1000 carbon atoms.

6. The dental floss of claim 5 in which the alpha-olefin is butene-1, 4-methylpentene-1, hexene-1, octene-1, or decene-1.

7. The dental floss of claim 5 in which the content of the alpha-olefin is 0.5 to 10 on an average per 1000 carbon atoms.

8. The dental floss of claim 5 in which the copolymer is an ultrahigh-molecular-weight ethylene/1-butene copolymer.

9. The dental floss of claim 5 in which the copolymer is an ultrahigh-molecular-weight ethylene/1-octene copolymer.

10. The dental floss of claim 5 in which the copolymer is an ultrahigh-molecular-weight ethylene/propylene copolymer.

11. The dental floss of claim 5 in which the copolymer is an ultrahigh-molecular-weight ethylene/4-methyl-1-pentene copolymer.

12. The dental floss of claim 5 in which the copolymer is an ultrahigh-molecular-weight ethylene/1-hexene copolymer.

13. The dental floss of claim 5 in which the copolymer is an ultrahigh-molecular-weight ethylene/1-decene copolymer.

14. The dental floss of claim 5 in which the copolymer is ultrahigh-molecular-weight ethylene/propylene/1-butene copolymer.

15. The dental floss of claim 5 in which the ethylene/alpha-olefin copolymer has an intrinsic viscosity of 7 to 30 dl/g.

16. An interdental cleaning tool comprising a dental floss comprising a drawn multifilament of an ultrahighmolecular-weight polyolefin having an intrinsic viscosity of at least 5 dl/g, which is stretched taut between protruding portions of the tool spaced from each other by a predetermined distance.

17. An interdental cleaning tool comprising a dental floss comprising a drawn multifilament of an ultrahigh-molecular-weight polyolefin having an intrinsic viscosity of at least 5 dl/g wherein the drawn multifilament is drawn at a draw ratio of 5 to 80, and which is stretched taut between protruding portions of the tool spaced from each other by a predetermined distance.

18. An interdental cleaning tool comprising a dental floss comprising a drawn multifilament of an ultrahigh-molecular-weight polyolefin having an intrinsic viscosity of at least 5 dl/g, which is stretched taut between protruding portions of the tool spaced from each other by a predetermined distance.

19. An interdental cleaning tool comprising a dental floss comprising a drawn multifilament of an ultrahigh-molecular-weight polyolefin having an intrinsic viscosity of 7 to 30 dl/g, which is stretched taut between protruding portions of the tool spaced from each other by a predetermined distance.

20. An interdental cleaning tool comprising a dental floss comprising a drawn multifilament of an ultrahigh-molecular-weight ethylene/alpha-olefin copolymer having an intrinsic viscosity of at least 5 dl/g and containing at least one alpha-olefin having at least 3 carbon atoms in an amount of 0.1 to 20 on an average per 1000 carbon atoms, which is stretched taut between protruding portions of the tool spaced from each other by a predetermined distance.

21. An interdental cleaning tool comprising a dental floss comprising a drawn multifilament of an ultrahigh-molecular-weight ethylene/alpha-olefin copolymer in which the alpha-olefin is selected from the group consisting of butene-1, 4-methylpentene-1, hexene-1, octene-1, and decene-1, and the copolymer has an intrinsic viscosity of at least 5 dl/g and contains said alpha-olefin in an amount of 0.1 to 20 on an average per 1000 carbon atoms, which is stretched taut between protruding portions of the tool spaced from each other by a predetermined distance.

22. An interdental cleaning tool comprising a dental floss comprising a drawn multifilament of an ultrahigh-molecular-weight ethylene/alpha-olefin copolymer having an intrinsic viscosity of at least 5 dl/g and containing at least one alpha-olefin having at least 3 carbon atoms in an amount of 0.5 to 10 on an average per 1000 carbon atoms, which is stretched taut between protruding portions of the tool spaced from each other by a predetermined distance.

23. An interdental cleaning tool comprising a dental floss comprising a drawn multifilament of an ultrahigh-molecular-weight ethylene/1-butene copolymer having an intrinsic viscosity of at least 5 dl/g and containing said 1-butene in an amount of 0.1 to 20 on an average per 1000 carbon atoms, which is stretched taut between protruding portions of the tool spaced from each other by a predetermined distance.

24. An interdental cleaning tool comprising a dental floss comprising a drawn multifilament of an ultrahigh-molecular-weight ethylene/1-octene copolymer having an intrinsic viscosity of at least 5 dl/g and containing said 1-octene in an amount of 0.1 to 20 on an average per 1000 carbon atoms, which is stretched taut between protruding portions of the tool spaced from each other by a predetermined distance.

25. An interdental cleaning tool comprising a dental floss comprising a drawn multifilament of an ultrahigh-molecular-weight ethylene/propylene copolymer having an intrinsic viscosity of at least 5 dl/g and containing said propylene in an amount of 0.1 to 20 on an average per 1000 carbon atoms, which is stretched taut between protruding portions of the tool spaced from each other by a predetermined distance.

26. An interdental cleaning tool comprising a dental floss comprising a drawn multifilament of an ultrahigh-molecular-weight ethylene/4-methyl-1-pentene copolymer having an intrinsic viscosity of at least 5 dl/g and containing said 4-methyl-1-pentene in an amount of 0.1 to 20 on an average per 1000 carbon atoms, which is stretched taut between protruding portions of the tool spaced from each other by a predetermined distance.

27. An interdental cleaning tool comprising a dental floss comprising a drawn multifilament of an ultrahigh-molecular-weight ethylene/1-hexene copolymer having an intrinsic viscosity of at least 5 dl/g and containing said 1-hexene in an amount of 0.1 to 20 on an average per 1000 carbon atoms, which is stretched taut between protruding portions of the tool spaced from each other by a predetermined distance.

28. An interdental cleaning tool comprising a dental floss comprising a drawn multifilament of an ultrahigh-molecular-weight ethylene/1-decene copolymer having an intrinsic velocity of at least 5 dl/g and containing said 1-decene in an amount of 0.1 to 20 on an average per 1000 carbon atoms, which is stretched taut between protruding portions of the tool spaced from each other by a predetermined distance.

29. An interdental cleaning tool comprising a dental floss comprising a drawn multifilament of an ultrahigh-molecular-weight ethylene/propylene/1-butene copolymer having an intrinsic viscosity of at least 5 dl/g and containing said 1-butene in an amount of 0.1 to 20 on an average per 1000 carbon atoms, which is stretched taut between protruding portions of the tool spaced from each other by a predetermined distance.

30. An interdental cleaning tool comprising a dental floss comprising a drawn multifilament of an ultrahigh-molecular-weight ethylene/alpha-olefin copolymer having an intrinsic viscosity of 7 to 30 dl/g and containing at least one alpha-olefin having at least 3 carbon atoms in an amount of 0.1 to 20 on an average per 1000 carbon atoms, which is stretched taut between protruding portions of the tool spaced from each other by a predetermined distance.

* * * * *